United States Patent [19]

Frank et al.

[11] Patent Number: 4,946,029
[45] Date of Patent: Aug. 7, 1990

[54] PURIFICATION OF CARBOXYLIC ESTERS WHICH CONTAIN ALDEHYDES, ACETALS AND/OR UNSATURATED COMPOUNDS

[75] Inventors: Gerhard Frank, Hirschberg; Hubert Lendle, Ludwigshafen; Wilfried Seyfert, Weisenheim; Peter Stops, Altrip, all of Fed. Rep. of Germany

[73] Assignee: BASF Aktiengesellschaft, Ludwigshafen, Fed. Rep. of Germany

[21] Appl. No.: 314,952

[22] Filed: Feb. 24, 1989

[30] Foreign Application Priority Data

Feb. 27, 1988 [DE] Fed. Rep. of Germany ....... 3806304

[51] Int. Cl.$^5$ .......................... B01D 3/34; C07C 67/54
[52] U.S. Cl. .......................... 203/29; 203/32; 203/34; 203/35; 203/38; 203/91; 203/74; 560/190; 560/191; 560/204; 560/248
[58] Field of Search .................. 203/32, 29, 34, 35, 203/49, 81, 82, 74, 75, 99, DIG. 19; 560/233, 248, 191, 190, 204, 1, 114, 122; 260/410.9 R, 420

[56] References Cited

U.S. PATENT DOCUMENTS

| | | |
|---|---|---|
| 4,189,599 | 2/1980 | Kesling et al. ................... 560/204 |
| 4,230,533 | 10/1980 | Giroux ....................... 203/DIG. 19 |
| 4,350,572 | 9/1982 | Kummer et al. ................... 203/35 |
| 4,360,692 | 11/1982 | Kummer et al. .................. 560/206 |
| 4,523,027 | 6/1985 | Kummer et al. .................. 560/191 |
| 4,586,987 | 5/1986 | Schneider et al. ................. 203/32 |
| 4,744,869 | 5/1988 | Saito et al. ...................... 203/82 |
| 4,802,956 | 2/1989 | Dornhagen et al. ....... 203/DIG. 19 |

FOREIGN PATENT DOCUMENTS

| | | |
|---|---|---|
| 101910 | 4/1985 | European Pat. Off. . |
| 62-153248 | 7/1987 | Japan ..................... 560/248 |

*Primary Examiner*—Wilbur Bascomb
*Attorney, Agent, or Firm*—Keil & Weinkauf

[57] ABSTRACT

Carboxylic esters obtained by reacting olefinically unsaturated compounds with carbon monoxide and alcohols and containing aldehydes, acetals and/or unsaturated compounds are purified by (a) treating the carboxylic ester which contains an aldehyde, acetal or unsaturated compound in a first stage at from 20° to 200° C. with a strongly acidic agent and (b) hydrogenating the mixture thus treated in a second stage at from 50° to 200° C. under a pressure of from 1 to 50 bar in the presence of one or more metals of subgroup VIII of the periodic table and (c) removing low and high boilers from the hydrogenated mixture obtained in stage b by distillation and obtaining a pure carboxylic ester.

4 Claims, No Drawings

PURIFICATION OF CARBOXYLIC ESTERS WHICH CONTAIN ALDEHYDES, ACETALS AND/OR UNSATURATED COMPOUNDS

The carbonylation of olefins, i.e. the reaction of for example ethylene, propylene or butylene with carbon monoxide and alkanols in the presence of carbonyl complexes of metals of group VIII of the periodic table, is used in industry on a large scale for producing carboxylic esters. If the starting materials used are diolefins, for example 1,3-butadiene, then dimethyl adipate, a useful starting material for producing fiber raw materials, is obtained via a pentenoic ester intermediate. Since carbon monoxide frequently contains hydrogen in small amounts or hydrogen forms by reaction with entrained water, a hydroformylation reaction takes place as well as the carbonylation reaction. This hydroformylation leads to aldehydes and, by reaction with alcohols present, to acetals. Furthermore, the synthesis gives rise to low concentrations of unsaturated ketones, tridecanones and butenedicarboxylic esters as byproducts. If the boiling points of the acetals, aldehydes, unsaturated ketones or butenedicarboxylic esters are very close to those of the esters produced, a distillative removal of these undesirable byproducts is technically extremely complicated. The removal of aldehydes, acetals and unsaturated compounds has special importance in the production of adipic esters, since the adipic acid produced therefrom is then less suitable for the production of polymers of fiber quality. In addition, even small amounts of aldehydes, acetals and unsaturated compounds cause undesirable discoloring in the products.

European Patent Specification No. 101,910 discloses a process where the purification of carboxylic esters which contain aldehydes, acetals and/or unsaturated compounds is performed by treating said esters in one step with hydrogen at elevated temperatures in the presence of an acidic ion exchanger or zeolite which contains one or more metals of subgroup VIII of the periodic table and removing the low and/or high boilers formed by distillation. This process has the disadvantage that the activity of the catalyst decreases, causing the level of impurities in the end product to rise.

It is an object of the present invention to provide a process which makes it possible to reduce the level of discoloring impurities and to improve catalyst life.

We have found that this object is achieved with a process for purifying a carboxylic ester which has been obtained by reacting an olefinically unsaturated compound with carbon monoxide and an alkanol and contains an aldehyde, an acetal or an unsaturated compound by treating said ester with an acidic agent and hydrogen in the presence of one or more metals of sub-group VIII of the periodic table and removing the low and/or high boilers formed by distillation, which comprises (a) treating the carboxylic ester which contains an aldehyde, acetal or unsaturated compound in a first stage at from 20 to 200° C. with a strongly acidic agent and (b) hydrogenating the mixture thus treated in a second stage at from 50 to 200° C. under a pressure of from 1 to 50 bar in the presence of one or more metals of sub-group VIII of the periodic table.

The novel process has the advantage that the proportion of discoloring impurities is appreciably reduced and, what is more, catalyst life is improved.

Preferred carboxylic esters are obtained by carbonylation of $C_2$–$C_{12}$-monoolefins, $C_4$–$C_{12}$-diolefins, $C_5$–$C_{12}$-cycloalkenes or $C_1$–$C_8$-alkyl $C_3$–$C_{12}$-alkenemonocarboxylates. The carbonylation is effected in a conventional manner by reaction with carbon monoxide and $C_1$–$C_8$-alkanols, in particular $C_1$–$C_4$-alkanols, for example at from 100 to 200° C. and at pressures of from 50 to 1,000 bar in the presence of carbonyl complexes of metals of subgroup VIII of the periodic table, in particular carbonyl complexes of cobalt or rhodium. The results are $C_3$–$C_{13}$-alkanemonocarboxylic esters of alkanols of from 1 to 8 carbon atoms, $C_6$–$C_{14}$-alkanedicarboxylic esters of alkanols of from 1 to 8 carbon atoms or cycloalkanecarboxylic esters of from 5 to 12 carbon atoms in the ring. Particular preference is given to saturated alkanemonocarboxylic and alkanedicarboxylic esters having the abovementioned numbers of carbon atoms. Esters prepared in this way contain aldehydes and acetals as byproducts, the aldehyde portion having the same number of carbons as the corresponding carboxylic acids. The acetals in addition contain those radicals which correspond to the alkanols used. Also present are unsaturated ketones or unsaturated dicarboxylic esters, depending on the type of starting material used. The level of aldehydes and acetals is for example from 0.1 to 15% by weight. Suitable methods are described for example in U.S. Pat. No. 3,176,028 and German Laid-Open Application DOS No. 1,618,156.

Particular industrial importance has been attained by $C_1$–$C_4$-alkyl adipates prepared by carbonylation of butadiene or $C_1$–$C_4$-alkyl pentenoates with carbon monoxide and $C_1$–$C_4$-alkanols. A typical mixture, in addition to adipic ester, contains for example from 9 to 14% by weight of methylglutaric ester, from 2 to 5% by weight of ethylsuccinic ester, from 0.01 to 0.3% by weight of 5-formylvaleric ester and from 0.01 to 0.5% by weight of 6,6-dimethoxycarboxylic ester. Suitable processes are described for example in German Patent No. 2,713,195.

According to the invention, the mixture to be purified is treated in a first stage at from 20 to 200° C. with a strongly acidic agent.

Suitable strongly acidic agents are for example sulfuric acid, phosphoric acid, benzenesulfonic acid and toluenesulfonic acid; preference is given to strongly acidic ion exchangers, for example crosslinked polystyrene having sulfonic acid groups, and also aluminum silicate or boron silicate zeolites in the acidic form. In the case of strongly acidic ion exchangers such as aluminum silicate or boron silicate zeolites, it is advantageous to use from 0.01 to 0.1 kg per kg of supplied starting mixture, whereas the remainder of the acidic agents mentioned are used in an amount of from 1 to 50% by weight, based on the amount of acetal. The reaction time is in general from 0.1 to 4 hours. Advantageously, a temperature of from 60 to 140° C. is maintained. However, if an acidic ion exchanger based on crosslinked polystyrene is used, 130° C. should not be exceeded.

It has further proved useful to strip out the alcohols formed in the treatment by treatment with inert gases, for example nitrogen. It has further proved useful to use water in small amounts, for example in an amount of from 0.5 to 2.0 moles per mole of acetal.

The mixture thus obtained is hydrogenated according to the invention in a separate second stage at from 50 to 200° C. under a pressure of from 1 to 50 bar in the presence of one or more metals of subgroup VIII of the periodic table.

Suitable metals are for example cobalt, nickel, palladium and rhodium. Particular preference is given to cobalt and palladium. The catalyst may be employed in the form of solid or supported catalysts. In the case of solid catalysts, such as cobalt or nickel, modification with promotors, for example manganese in an amount of from 2 to 5% by weight, based on cobalt or nickel, and/or the modification with phosphoric acid, for example from 1 to 4% by weight of phosphoric acid (calculated as $P_2O_5$), based on cobalt and/or nickel, have proved useful. If a supported catalyst is employed, suitable supports are for example silicon dioxide, aluminum oxide, activated carbon and silicates.

The supported catalyst advantageously contains from 0.2 to 5% by weight, in particular from 0.2 to 2% by weight, of the metals mentioned.

The hydrogenation is carried out at from 50 to 200° C., advantageously at from 100 to 170° C., under a pressure of from 1 to 50 bar, preferably from 10 to 30 bar. The residence time is preferably from 0.3 to 3 hours.

The hydrogenated mixture thus obtained is distilled to separate the high and low boilers from the carboxylic ester.

Advantageously, the distillation is carried out by separating the low and high boilers from the carboxylic ester by distillation in two columns connected in series, the high boilers being removed in the first column as bottom product and the mixture of low boilers and carboxylic ester being withdrawn at the top of the column and, in the second column, the low boilers being separated from this mixture as heads and the carboxylic ester being withdrawn in the bottom part of the column. In general, the mixture to be separated is fed into the middle third portion of the respective column. The pure carboxylic ester is advantageously removed from the second column at the base thereof, in particular at a point from 1 to 5 theoretical plates above the base.

It is advantageous to use columns containing packing, bubble cap trays or sieve trays, in particular structured packing ensuring a pressure drop per tray of less than 2.5 mbar. Preferably, the columns have from 40 to 120 theoretical plates. In addition, it has proved useful to maintain a reflux ratio of from 1 to 10.

In a modified procedure, the carboxylic ester which contains low and high boilers is introduced into the central part of the first column, low boilers are removed at the head of the column, high boilers are separated off at the base of the column, a portion of the vaporous mixture is removed in the lower third of the column and passed into the lower end of the second column, pure carboxylic ester is removed in the central portion of the second column, and the vaporous mixture is recycled from the top of the second column back into the upper third portion of the first column.

In a particularly advantageous embodiment, the low and high boilers are separated from the carboxylic ester by distillation in a column, the mixture to be separated being introduced into the bottom half of the column, carboxylic ester being removed as a sidestream in the upper half of the column, and low boilers being removed at the top of the column and higher boilers at the base of the column.

Preference is given to using a column with internal fitments as described above, which has from 60 to 150 theoretical plates. The mixture to be separated is advantageously introduced into the second quarter (counted from the bottom end) of the column. Pure carboxylic ester is removed as a sidestream in the upper half of the column, for example from the third quarter (counted from the bottom end). A reflux ratio, based on the side takeoff weight, of from 2 to 10 has proved useful.

In a modified procedure, the low and high boilers are separated from the carboxylic ester by distillation in a column, the mixture to be separated being introduced into the second quarter of the column, carboxylic ester being removed sideways in the third quarter of the column and low boilers being removed at the head of the column and high boilers at the base of the column, the column having been split lengthwise in two zones in the middle two thirds, with the proviso that the feed is passed into the first zone and carboxylic ester is removed from the second zone.

The esters purified according to the invention are suitable for use as solvents. Adipic esters are hydrolyzed to adipic acid, which is a starting material for producing polycondensates, such as nylon-6.6.

The process according to the invention may be illustrated by the following examples:

COMPARATIVE EXAMPLE 1

A 40 liter capacity tubular reactor packed with a strongly acidic ion exchanger based on polystyrene having sulfonic acid groups and containing 5 g of palladium per liter of ion exchanger is fed per hour with 13 kg of dimethyl adipate which contains 0.15% by weight of methyl 6,6-dimethoxycaproate, 0.03% by weight of dimethyl butene-dicarboxylate, 0.03% by weight of tridecanone, 0.2% by weight of dimethyl 2-methylglutarate and traces of methyl 5-formylvalerate and has a UV number of 19,000 together with 50 liters (S.T.P.) of hydrogen. The mixture is hydrogenated at 110° C. under a pressure of 30 bar. The output from the reaction is let down and rectified. The pure product thus obtained contains 99.74% by weight of dimethyl adipate and has a UV number of 1,100. In the course of 400 hours of operation, the UV number rises to 1,310.

EXAMPLE 1

A 40 liter capacity tubular reactor packed with Y-zeolite in the $H^+$ form is fed per hour with 13 kg of dimethyl adipate which contains 0.15% by weight of methyl 6,6-dimethoxycaproate, 0.03% by weight of methyl butene-dicarboxylate, 0.03% by weight of tridecanone, 0.2% by weight of dimethyl methylglutarate and traces of methyl formylvalerate and has a UV number of 19,000, and the contents are treated at 120° C.

In a second stage, the output thus obtained is fed into a second 40 liter capacity reaction tube, charged with alumina containing 0.7% by weight of palladium, together with 50 liters (S.T.P.) of hydrogen, and the hydrogenation is carried out at 135° C. under a pressure of 30 bar. The output obtained is let down and freed from low and high boilers by distillation. The rectification gives 99.8% by weight of dimethyl adipate having a UV number of 900. Following 400 hours of operation, there is no sign of the hydrogenation catalyst becoming deactivated.

EXAMPLE 2

Example 1 is repeated in that impure dimethyl adipate is treated with Y-zeolite in the H form.

A tube (internal diameter 2.5 cm, height 15 cm) which is heatable via a jacket is charged with 80 ml (= 130 g) of a cobalt catalyst, reduced at 330° C. with $H_2$, in chip form (1–2 mm). Before the reduction of the oxidic catalyst the composition of the catalyst was 90.40% of CoO, 5.04% of $Mn_2O_3$, 2.22% of $P_2O_5$ and 1.40% of $Na_2O$. The catalyst is 80% reduced, based on cobalt and manganese. 300 ml of crude dimethyl adipate, pretreated as in Example 1, are passed per hour over this catalyst at 120° C. and 20 bar $H_2$. Fractional distillation of the output from the reductive aftertreatment gave a main fraction (98%) having a UV number of 300.

The components responsible for the UV number were predominantly in the first cut.

After 1,000 hours there is no sign of any loss of catalyst activity.

COMPARATIVE EXAMPLE 2

The apparatus described in Example 2 is charged with 80 ml of a zeolite containing 0.5% of palladium. Following activation of the catalyst with hydrogen, 300 ml of the acetal-containing crude dimethyl adipate was introduced per hour at 120° C. and 20 bar $H_2$.

The starting material is dimethyl adipate having a UV number of 12,498. Following a similar fractional distillation of the hydrogenation output the UV number is 1,200. The components responsible for the UV number are predominantly in the tailings.

After 48 hours the activity of the catalyst decreases appreciably.

COMPARATIVE EXAMPLE 3

Following an acidic and hydrogenating treatment of a dimethyl adipate as described in Example 1 the reaction mixture is separated in a two-stage distillation. The feed is into the bottom part of the first column, which is equipped with 70 theoretical plates. There the low-boiling impurities are separated off overhead under a reflux ratio of 10. The main stream obtained at the base of this vacuum column at 160° C., is subsequently distilled again by introducing it into the bottom part of a vacuum column (60 mbar) of 90 theoretical plates. Using a reflux ratio of 2.5, a purified ester mixture having a UV number of 1,250 is obtained overhead.

EXAMPLE 3

If the distillative workup of the acidically and hydrogenatingly treated dimethyl adipate (see Example 1) is carried out in a single stage by introducing the reaction mixture into the bottom part of a column of 100 theoretical plates and withdrawing the useful product as a sidestream in the upper half, this useful product, at a reflux ratio of 4, based on the side takeoff, is obtained with a UV number of 900. The distillation carried out under reduced pressure ends with the base of column temperature of 165° C.

We claim:

1. A process for purifying $C_1$–$C_4$-alkyl adipates prepared by carbonylation of butadiene or $C_1$–$C_4$-alkyl pentenoates with carbon monoxide and $C_1$–$C_4$-alkanols, and containing color formers, including aldehydes, acetals and unsaturated dicarboxylic acids, comprising the following steps:
   (a) contacting the $C_1$-to-$C_4$-alkyl adipates containing such color formers with a strongly acidic agent at from 20 to 200° C. for a period of from 0.1 to 4 hours, while stripping off the $C_1$-to-$C_4$-alkanols formed,
   (b) contacting the $C_1$-to-$C_4$-alkyl adipates obtained in step (a) in a separate and subsequent stage with hydrogen at from 50 to 200° C. under a pressure of from 1 to 50 bar in the presence of one or more metals of subgroups VIII of the periodic table for a period of from 0.3 to 3 hours, and
   (c) purifying the $C_1$-to-$C_4$-alkyl adipates obtained in step (b), by fractional distillation, while removing low and high boilers.

2. A process as described in claim 1, wherein the acidic agent is a Y zeolite in the acidic form.

3. A process as described in claim 1, wherein the metal is a palladium catalyst.

4. A process as described in claim 1, wherein the metal is a cobalt catalyst.

* * * * *